United States Patent
Rao et al.

(10) Patent No.: US 12,201,403 B2
(45) Date of Patent: Jan. 21, 2025

(54) FREE FLOW FEVER SCREENING

(71) Applicant: NEC Laboratories America, Inc., Princeton, NJ (US)

(72) Inventors: Kunal Rao, Monroe, NJ (US); Giuseppe Coviello, Princeton, NJ (US); Min Feng, Monmouth Junction, NJ (US); Biplob Debnath, Princeton, NJ (US); Wang-pin Hsiung, Santa Clara, CA (US); Murugan Sankaradas, Dayton, NJ (US); Srimat Chakradhar, Manalapan, NJ (US); Yi Yang, Princeton, NJ (US); Oliver Po, San Jose, CA (US); Utsav Drolia, Milipitas, CA (US)

(73) Assignee: NEC Corporation, Tokyo (JP)

( * ) Notice: Subject to any disclaimer, the term of this patent is extended or adjusted under 35 U.S.C. 154(b) by 342 days.

(21) Appl. No.: 17/325,613

(22) Filed: May 20, 2021

(65) Prior Publication Data

US 2021/0378520 A1 Dec. 9, 2021

Related U.S. Application Data

(60) Provisional application No. 63/031,892, filed on May 29, 2020.

(51) Int. Cl.
*A61B 5/01* (2006.01)
*A61B 5/00* (2006.01)

(52) U.S. Cl.
CPC .............. *A61B 5/01* (2013.01); *A61B 5/7264* (2013.01); *A61B 5/742* (2013.01); *A61B 5/746* (2013.01)

(58) Field of Classification Search
CPC ......... A61B 5/01; A61B 5/7264; A61B 5/742; A61B 5/746
See application file for complete search history.

(56) References Cited

U.S. PATENT DOCUMENTS 10,085,006 B2 * 9/2018 Ho ..................... H04N 13/111
2015/0281749 A1 * 10/2015 Hutchison ............... G06T 5/001
348/164

(Continued)

OTHER PUBLICATIONS

Haghmohammadi et al. "Remote measurement of body temperature for an indoor moving crowd", 2018 IEEE International Conference on Automation, Quality and Testing, Robotics (AQTR). May 24, 2018. pp. 1-6.

(Continued)

*Primary Examiner* — Devin B Henson
*Assistant Examiner* — Evelyn Grace Park
(74) *Attorney, Agent, or Firm* — Joseph Kolodka

(57) ABSTRACT

A method for free flow fever screening is presented. The method includes capturing a plurality of frames from thermal data streams and visual data streams related to a same scene to define thermal data frames and visual data frames, detecting and tracking a plurality of individuals moving in a free-flow setting within the visual data frames, and generating a tracking identification for each individual of the plurality of individuals present in a field-of-view of the one or more cameras across several frames of the plurality of frames. The method further includes fusing the thermal data frames and the visual data frames, measuring, by a fever-screener, a temperature of each individual of the plurality of individuals within and across the plurality of frames derived from the thermal data streams and the visual data streams, and generating a notification when a temperature of an individual exceeds a predetermined threshold temperature.

16 Claims, 8 Drawing Sheets

(56) References Cited

U.S. PATENT DOCUMENTS

| | | | |
|---|---|---|---|
| 2015/0324656 A1* | 11/2015 | Marks | G06V 40/10 |
| | | | 383/103 |
| 2023/0043342 A1* | 2/2023 | Tremblay | H04N 23/698 |

OTHER PUBLICATIONS

Negishi et al. "Contactless Vital Signs Measurement System Using RGB-Thermal Image Sensors and Its Clinical Screening Test on Patients with Seasonal Influenza", Sensors vol. 20, No. 8. Apr. 13, 2020. pp. 1-16.

Negishi et al., "Stable Contactless Sensing of Vital Signs Using RGB-Thermal Image Fusion System with Facial Tracking for Infection Screening", 40th Annual International Conference of the IEEE Engineering in Medicine and Biology Society (EMBC). Jul. 18, 2018. pp. 1-4.

Somboonkaew et al., "Mobile-platform for automatic fever screening system based on infrared forehead temperature". 2017 Opto-Electronics and Communications Conference (OECC) and Photonics Global Conference (PGC). Jul. 31, 2017. pp. 1-4.

Sun et al., "Applications of Infrared Thermography for Noncontact and Noninvasive Mass Screening of Febrile International Travelers at Airport Quarantine Stations", Application of Infrared to Biomedical Sciences. Research Gate—Downloaded Sep. 6, 2020. pp. 347-358.

Sun et al., "Remote sensing of multiple vital signs using a CMOS camera-equipped infrared thermography system and its clinical application in rapidly screening patients with suspected infectious diseases", International Journal of Infectious Diseases. vol. 55. Jan. 2017. pp. 113-117.

Tay et al., "Comparison of Infrared Thermal Detection Systems for mass fever screening in a tropical healthcare setting", Public Health. vol. 129, No. 11. Nov. 2015. pp. 1471-1478.

Thermoworks, "Infrared Emissivity Table", https://www.thermoworks.com/emissivity-table. Last accessed May 19, 2021. pp. 1-8.

Yao et al., "Multiple Vital-Sign-Based Infection Screening Outperforms Thermography Independent of the Classification Algorithm", IEEE Transactions on Biomedical Engineering. vol. 63, No. 5. May 2016. pp. 1025-1033.

\* cited by examiner

FREE FLOW FEVER SCREENING

RELATED APPLICATION INFORMATION

This application claims priority to Provisional Application No. 63/031,892, filed on May 29, 2020, the contents of which are incorporated herein by reference in their entirety.

BACKGROUND

Technical Field

The present invention relates to fever screening and, more particularly, to methods and systems related to free flow fever screening.

Description of the Related Art

One of the common symptoms for a person infected with a virus, e.g., COVID-19, is fever. Reliable and accurate detection of fever helps in isolating potentially infected/sick people. Conventional fever screening solutions expect that an individual walks to a kiosk, pauses or stops at the kiosk for a while, poses at the kiosk to get his/her temperature measured and then proceeds. This process is too slow and reduces the overall throughput, that is, the number of people that can enter the area per minute. Also, if there are too many people trying to enter, then soon it might create a bottleneck and people might start gathering behind to get in, resulting in people coming in close contact, which increases the risk of getting infected by the virus.

SUMMARY

A method for free flow fever screening by measuring core body temperature of individuals from a distance without human intervention is presented. The method includes capturing, by one or more cameras, a plurality of frames from thermal data streams and visual data streams related to a same scene to define thermal data frames and visual data frames, detecting and tracking, by a person tracker, a plurality of individuals moving in a free-flow setting within the visual data frames, generating a tracking identification (id) for each individual of the plurality of individuals present in a field-of-view of the one or more cameras across several frames of the plurality of frames, fusing, by a frame fuser, the thermal data frames and the visual data frames temporally and spatially, measuring, by a fever-screener, a temperature of each individual of the plurality of individuals within and across the plurality of frames derived from the thermal data streams and the visual data streams, and generating a notification when a temperature of an individual of the plurality of individuals exceeds a predetermined threshold temperature.

A non-transitory computer-readable storage medium comprising a computer-readable program for free flow fever screening by measuring core body temperature of individuals from a distance without human intervention is presented. The computer-readable program when executed on a computer causes the computer to perform the steps of capturing, by one or more cameras, a plurality of frames from thermal data streams and visual data streams related to a same scene to define thermal data frames and visual data frames, detecting and tracking, by a person tracker, a plurality of individuals moving in a free-flow setting within the visual data frames, generating a tracking identification (id) for each individual of the plurality of individuals present in a field-of-view of the one or more cameras across several frames of the plurality of frames, fusing, by a frame fuser, the thermal data frames and the visual data frames temporally and spatially, measuring, by a fever-screener, a temperature of each individual of the plurality of individuals within and across the plurality of frames derived from the thermal data streams and the visual data streams, and generating a notification when a temperature of an individual of the plurality of individuals exceeds a predetermined threshold temperature.

A system for free flow fever screening by measuring core body temperature of individuals from a distance without human intervention is presented. The system includes one or more cameras to capture a plurality of frames from thermal data streams and visual data streams related to a same scene to define thermal data frames and visual data frames, a person tracker to detect and track a plurality of individuals moving in a free-flow setting within the visual data frames, a tracking identification (id) generated for each individual of the plurality of individuals present in a field-of-view of the one or more cameras across several frames of the plurality of frames, a frame fuser to fuse the thermal data frames and the visual data frames temporally and spatially, and a fever-screener to measure a temperature of each individual of the plurality of individuals within and across the plurality of frames derived from the thermal data streams and the visual data streams, wherein a notification is generated when a temperature of an individual of the plurality of individuals exceeds a predetermined threshold temperature.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
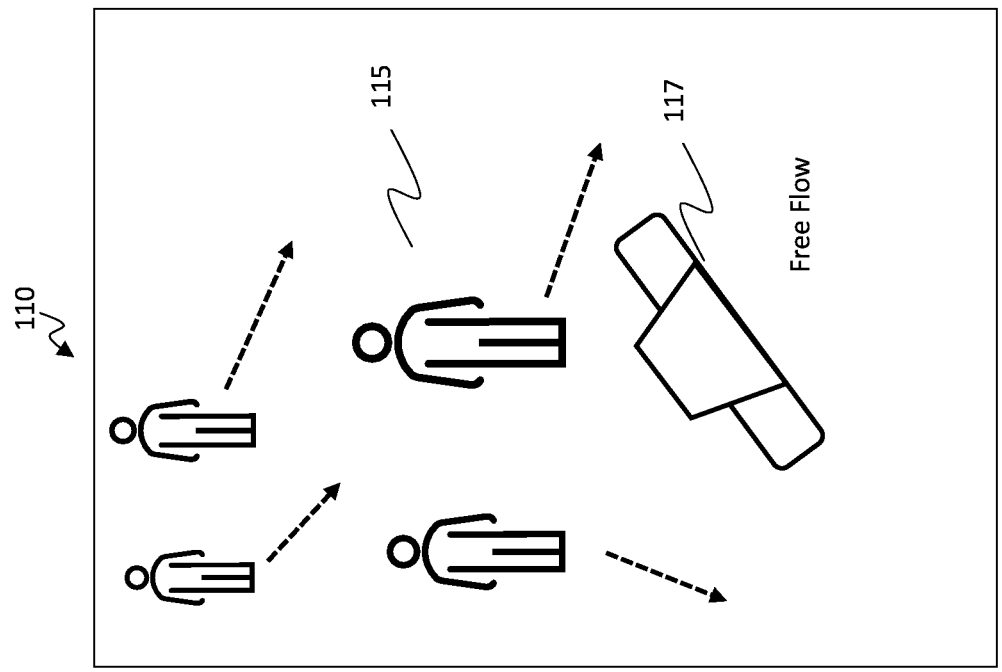
FIG. 1 is a block/flow diagram of an exemplary pause-and-go configuration versus an exemplary free flow configuration, in accordance with embodiments of the present invention.
Figure 1:
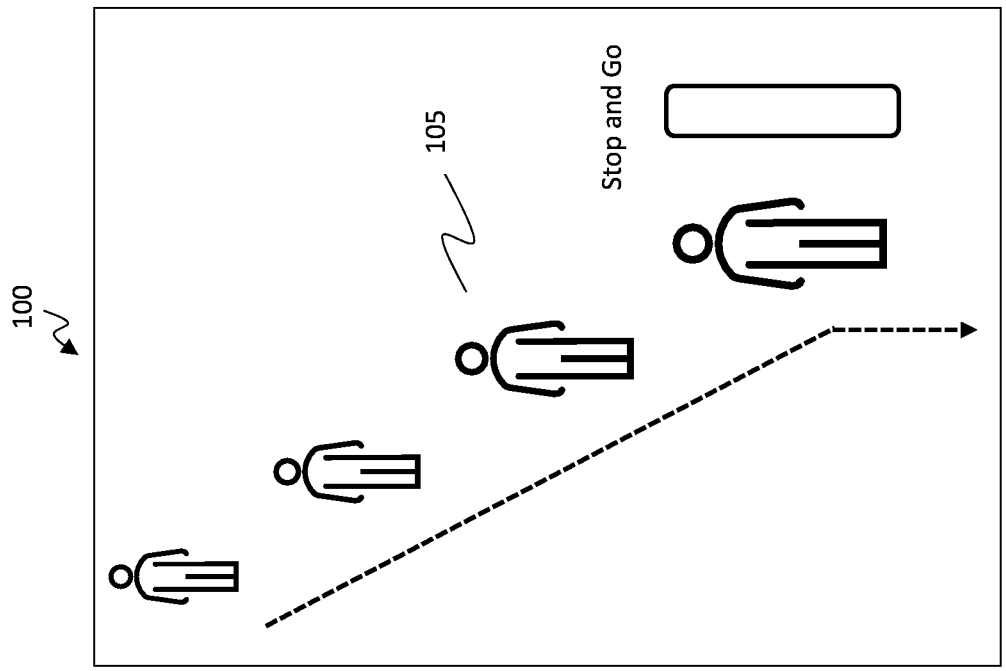

Coronavirus Disease 2019, abbreviated as COVID-19 is a respiratory disease caused by a novel coronavirus named SARS-CoV-2. This virus has its origin in bats and initial outbreak of this disease among humans was first observed in December 2019 in Wuhan, Hubei Province in China. Many of the early patients were reported to have some links to live animal markets a.k.a. wet markets, suggesting its transmission from animal-to-person. Subsequently, the disease was reported even in people who did not have any direct connection to the wet markets, indicating some sort of person-to-person transmission. This person-to-person transmission caught up quickly and many cases started being reported within and outside of Wuhan and soon across entire China, and then other nations. Community spread also started showing up in several locations. Within a matter of weeks, the virus spread to hundreds of other countries and a global outbreak led to the COVID-19 pandemic.

Based on the current understanding of the nature of this virus, it has been observed that the virus has a very high reproductive number (RO value) and can spread very quickly from person-to-person through respiratory droplets produced by an infected person. People without any symptoms can also spread the virus to others and the effects of the illness caused by this virus could range anywhere from mild to severe and can even lead to death. People at higher risk of severe illness include people above 65 years of age, people living in nursing homes and long-term care facilities and people of all ages with serious underlying medical conditions as per the Center for Disease Control and Prevention (CDC). Spread of the virus is more likely when people are in close contact and within 6 to 8 feet distance from one another, where the respiratory droplets produced by an infected person could get into the mouth or nose of a healthy person. These respiratory droplets can also land on surfaces and could spread through surface contact by healthy individuals.

Due to the nature of spread of the virus and how quickly it can spread, several countries declared a "national emergency" and issued "stay-at-home" orders to force people to stay indoors and shutdown all non-essential businesses to contain the spread, so as to avoid overwhelming the healthcare system. Some of the measures to contain the spread include quick identification and isolation of infected individuals, tracing of people who might have come in contact with infected individuals a.k.a. contact tracing, maintaining 6 to 8 feet distance between people a.k.a. social distancing, avoiding crowded and public places, wearing face cloth covering when outside, and following proper hygiene, which includes frequently washing hands with soap and water.

While it would be ideal to keep people distant from each other in order to defeat this virus, it is not practical to keep doing this for a long term over several months and years due to the adverse effects it has on the economy and the mental health of people. To strike a balance between health of people and the economic conditions, countries are cautiously trying to re-open parts of the economy so that some sort of normalcy can be achieved where people can get back to work and do business to some extent. Given that countries are already taking such actions to re-open the economy, it is inevitable that techniques are needed that aid people in following the guidelines and provide tools and technology to identify and isolate individuals so that the healthy population and infected population can be kept separate.

Regarding free flow fever screening, as noted, one of the common symptoms for a person infected with COVID-19 is fever. Reliable and accurate detection of fever helps in isolating potentially infected people. $F^3S$ is introduced herein, which screens for people with fever as people move in a free flow setting. By free flow, it is meant that individuals need not pause or stop to get their temperature measured. Conventional fever screening solutions expect that the individual walks to a kiosk, pauses or stops there for a while, poses at the kiosk to get a temperature measurement, and then proceeds. This process is too slow and reduces the overall throughput, that is, number of people that can enter the area per minute. Also, if there are too many people trying to enter, then soon it might create a bottleneck and people might start gathering behind to get in, resulting in people coming in close contact, which increases the risk of getting infected.

To avoid this, a beneficial and advantageous process would allow people to walk through without pausing or stopping and temperatures would be measured for all individuals as they walk normally, that is, in free flow movement. FIG. 1 shows a setup where people 105 need to pause or stop (diagram 100), get their temperature measured and then proceed, and further shows the free flow movement of people (diagram 110), where temperature is measured as people 115 walk through, thereby increasing the overall throughput. One or more cameras 117 can aid in the detection and tracking of people 115. $F^3S$ proves to be beneficial for monitoring people with fever and isolating potentially infected individuals.

The exemplary embodiments of the present invention present $F^3S$, a free flow fever screening solution which enables real-time, high-throughput measurement of core body temperature of individuals from a distance without any human intervention. The exemplary embodiments present techniques to fuse thermal frames with visual frames to enable accurate temperature measurement of multiple individuals simultaneously within and across frames. The exemplary embodiments present techniques to measure temperature of individuals across frames, at different regions (eyes, face and head) depending on visibility, prioritize them, revise them, calculate a final reading across multiple readings and suppress repeated alerts for a same individual. The exemplary embodiments further present techniques to measure temperature of individuals even when their face cannot be detected due to masks, sunglasses, hats, or if the face is at an angle, etc. The exemplary embodiments present a methodology to perform ground truth using thermal sensor data with visual sensor data to verify accuracy and correctness of temperature measurements of $F^3S$.

Fever screening involves measuring the core body temperature of individuals as they walk into a facility and triggers an alert when the temperature is found to be above a certain predetermined threshold, which is usually the temperature at which a person is considered to have a fever (CDC recommends this to be at 100.4 degrees Fahrenheit). Unlike other fever screening solutions, $F^3S$ is designed to operate in a free flow manner, that is, individuals are not required to pause or stop at specific choke points for the temperature to be measured. Instead, individuals can just keep walking as they normally do and their temperatures are measured automatically by the system from a distance as they cross the area. The system does not require any human intervention, which is a key concern for COVID-19 since it can spread through close contact of individuals.

Diagram 110 of FIG. 1 shows the setup for deployment of the $F^3S$. Arrows show the direction of movement of people from the entrance into, e.g., building. $F^3S$ is located further away from the entrance with the cameras pointing towards the entrance so that a large enough field-of-view is captured by the camera. As people walk into the building, their temperatures are measured and displayed on the screen for an operator to monitor. Temperature for a person in different parts of the body is different and it is found that the temperature around the eyes is less affected (than other parts of the body) due to ambient temperature and is close to the core body temperature. The exemplary embodiments measure temperature at this part, if possible, or nearby areas, if the individual is wearing glasses and temperature readings at the eyes is not possible.

If the temperature of a person is above a predetermined threshold, then an alert is triggered, and the operator can request the individual to step aside and proceed for secondary screening. The system acts as an initial screening solution and a final screening is performed using a medical device. Physical distance between operator and individuals is constantly maintained, as the operator does not need to come in close contact with the people. In fact, the operator need not be present at the location physically as well. Instead, everything can be monitored from a central location in a control room and if an alert is triggered, the individual can be notified over an audio speaker to step aside, thereby avoiding the need for any human to physically intervene.

Initially, only thermal sensor data was used to detect individuals and measure their temperatures, but it was discovered that the accuracy of detection and tracking using this technique is not very good, leading to poor temperature measurement for the individual. Along the same lines, in just using thermal sensor data, some cameras allow marking of regions within the frame and configure alerts to be triggered when the temperature in specific regions go above a certain threshold, but these techniques require further analysis to detect individuals within that region and doing so, using just thermal sensor data is inaccurate.

To overcome the above limitations, visual sensor data was combined with thermal sensor data to get accurate readings of the temperature for a person. Visual sensor data from thermal cameras are usually high resolution whereas the thermal sensor data is relatively low resolution. The exemplary embodiments use the high-resolution visual sensor data to detect and track individuals across frames and locate the eyes, if possible, or nearby areas and then co-relate this with the thermal sensor data at those locations to determine the temperature of the individual. It is noted that while detecting and tracking individuals, the exemplary methods try to do their best in obtaining temperature at the eyes. This may or may not be possible always, since people might be wearing masks, sunglasses, hats, etc., thereby occluding this portion of the face. Besides, people may be talking to one another while walking or looking down at mobile phones, etc., in which case it may not even be possible to detect the face and locate the eyes. To avoid missing temperature reading of an individual in such scenarios, and to avoid asking them to stop and obstruct the flow, the exemplary embodiments perform multiple levels of detections for individuals, such as body, head and face. Based on these multiple levels of detection and tracking, the exemplary embodiments measure the most accurate temperature possible for the individual across frames and determine final temperature for the person as he/she walks through.

Figure 2:
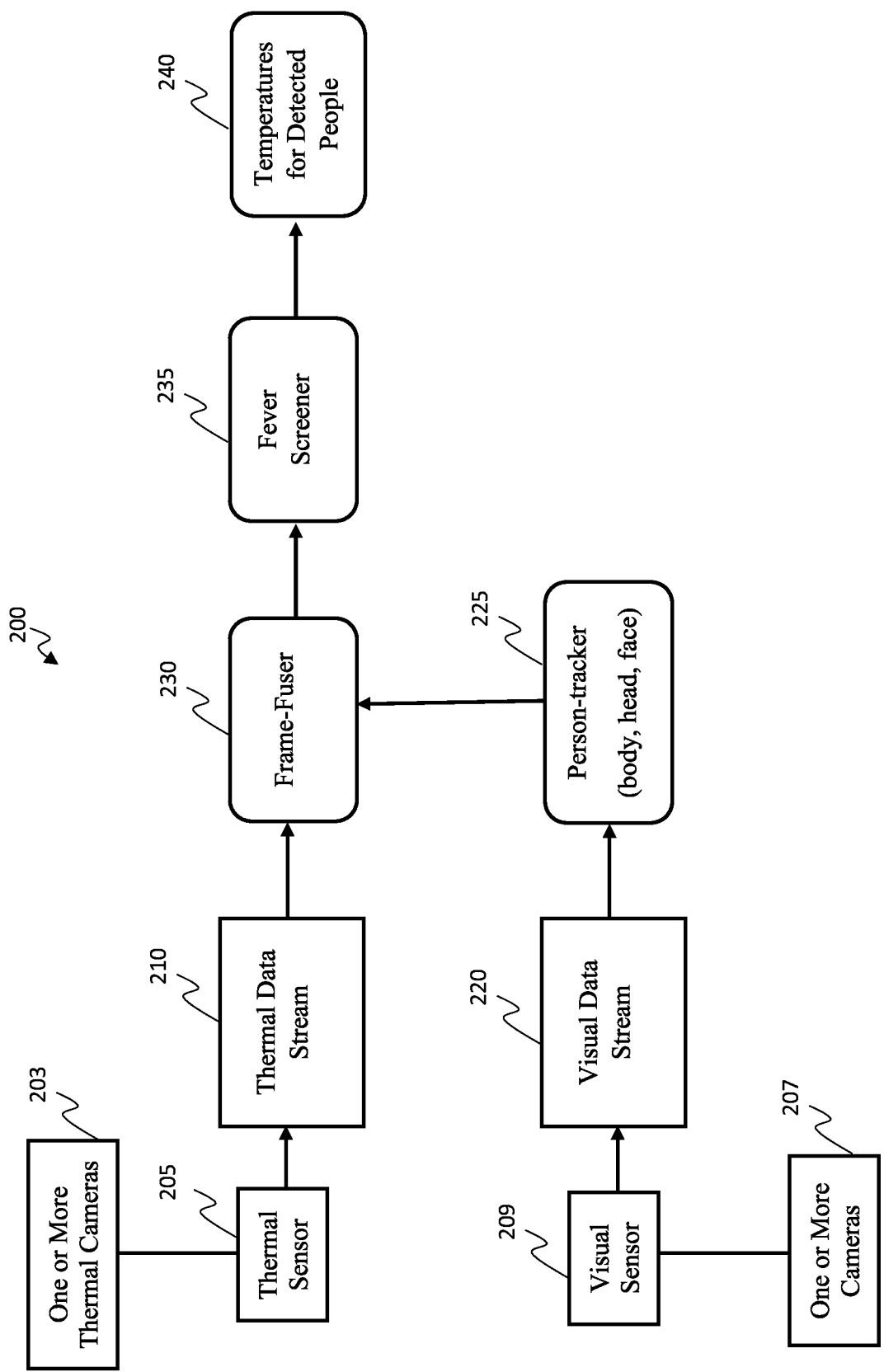
FIG. 2 is a block/flow diagram of an exemplary high-level system architecture for free flow fever screening, in accordance with embodiments of the present invention.

FIG. 2 shows a high-level system architecture 200 of $F^3S$. There are two streams of data coming into the system, that is, thermal data stream 210 and visual data stream 220. Both streams of data 210, 220 relate to a same scene, one including the visual RGB frame and the other including the thermal frame of the scene. Both these frames have different resolutions and potentially slightly different timestamps. One or more thermal cameras 203 can employ thermal sensors 205 to generate the thermal data stream 210, whereas one or more cameras 207 can employ visual sensors 209 to generate the visual data stream 220. Of course, one or more cameras can be employed which include both thermal sensors 205 and visual sensors 209.

The visual frame is processed by the person-tracking module/component (or person tracker 225) to detect and track body, head and face of the person. When the person is seen for the first time, a new tracking id is automatically generated for the person and while he/she is present in the field-of-view of the camera across frames, the tracking id of the person is maintained and emitted as part of the output. For each frame, this component/tracker 225 detects the bounding boxes of body, head and face of all the people in the frame. For a face, the location of eyes is also detected. Note that as the person enters the scene and while he/she is present in the scene, for different frames, none, or one or more of body, head and face of the person might be detected. The face might not be detected in cases when the person is wearing masks, sunglasses, hat, etc. or if the face is at an angle or occluded by something. The head and body might not be detected when the person is occluded by other individuals or large objects, such as a door. Depending on whatever can be detected for the person, this component/tracker 225 emits the visual frame along with detected bounding boxes and the tracking id for the individual.

The thermal frame and the output from person-tracking module/component 225 is processed by frame-fusion module/component (or frame fuser 230) to fuse the thermal and visual frames 210, 220 both temporally and spatially. Temporal fusion relates to fusing them in the time domain while spatial fusion relates to fusing them in the space domain. If the source of the thermal and visual frames is the same, then they both usually have the same timestamp and temporal fusion is simply matching the timestamp of the two frames. If the source is different and they may not have the exact same timestamp, then the one closest within a window is chosen and used to synchronize temporally. Spatial fusion relates to mapping of the pixels between the thermal and the visual frames. Once the bounding boxes are located in the visual frame, the temperature corresponding to the associated region needs to be obtained from the thermal frame. This spatial association and mapping between pixels is performed by frame-fusion module/component (frame fuser 230) and further used by fever screening module/component (fever screener 235) to determine the temperature 240.

Fever-screening module/component 235 receives and processes the output from the frame-fusion to detect temperatures 240 of individuals and to provide an alert or notification when the temperature exceeds a predetermined threshold temperature. To determine the temperature of individuals, fever-screening module/component (fever screener 235) maintains a cache of recently seen individuals along with their tracking id and bounding boxes of detections. When an individual is seen for the first time, he/she is added in the cache and depending on which detections (body, head and/or face) are available for the individual, the most accurate one is chosen and the temperature in that region is measured and recorded for the individual. While measuring the temperature, first priority is given to eye region, then to face region and finally to the head region. The tracking id is used to identify the same individual across multiple frames and temperature readings for the individual are measured, recorded, and updated in cache. This creates a cluster of temperature readings for the individual and by using these, a final temperature reading for the person is calculated and reported by the fever-screening module/component 235.

Regarding person tracking, the exemplary embodiments have a person detector or operator who can detect three objects, that is, face, head and body. In addition to the person detector or operator, a person tracking module/component (person tracker 225) has been developed. Person tracking is beneficial to achieve high accuracy and high usability. First, with person tracking, the exemplary embodiments can find the best (or more accurate) temperature of a person across different frames (e.g., sequential or consecutive frames). For instance, when a person starts with a long distance to the camera, and then walks close to the camera, the system detects multiple temperatures for the person in different frames. Without tracking, a large number of alerts will be sent to the operator who is using the system, making the system unusable due to inconsistent temperatures and a flooding of alerts. With person tracking, the system can find the best shot based on information such as the width of a face, head or body. Second, person tracking can combine the face, head, and body information. The face is most reliable for person recognition compared to the head and body, while the exemplary embodiments still need to use the head and body in a worst-case scenario. Since the person tracking can assign a single track id to the body, head, and face of a single person, the system can switch to the face when the face becomes available for the person.

A person tracking algorithm has been implemented in Algorithm 1. As shown in Algorithm 1, reproduced below, for each frame, the exemplary methods have a set of body, head, and face detected using the person detector 225. In the meantime, the system maintains a cache, namely, a person cache. The person cache includes a set of persons shown in the history files and each person has a unique id. The cache has the latest locations and snapshots of the head, body and face for each person. In Algorithm 1, the first loop performs a check for each incoming body with the person cache. The check includes both location calculation and image similarity.

```
Data: Body, Head, Face in frame
Result: Body with track id
/* process detected body                          */
foreach detected body do
|   if body matches any body in person cache then
|   |   assign the id in cache to the body;
|   else
|   |   assign a new id to the body;
|   end
end
/* process detected faces                         */
foreach detected face do
|   if face matches a face in person cache then
|   |   assign the id of the cache to the face;
|   |   if face in a body then
|   |   |   assign the id of the face to the body;
|   |   end
|   else
|   |   if face in a body then
|   |   |   assign the id in body to the face;
|   |   else
|   |   |   assign a new id to the face;
|   |   end
|   end
end
/* process detected heads                         */
foreach detected head do
|   if a face in the head then
|   |   assign the id of the face to the head;
|   else
|   |   if the head in a body then
|   |   |   assign the id in body to the head;
|   |   else
|   |   |   assign a new id to the head;
|   |   end
|   end
end
```

In other words, if two bodies in consecutive frames have close locations and high similarity score, these two bodies will have a same track id. In the second loop, the exemplary embodiments perform similarity calculation for an incoming face with faces in the person cache. Since a face match has very high accuracy, the exemplary embodiments give a high priority to a face match over a body match. If an incoming face is in an incoming body and the incoming face has a track id in the person cache, the exemplary embodiments will use the track id of the face for the incoming body as well. The exemplary embodiments assign a new id to a face if the face has neither a face match with the person cache nor a location match for incoming bodies. The third loop checks an incoming head with incoming faces and bodies and tries to find an id of faces or bodies for the head region. The exemplary embodiments do not use image similarity and location match across frames for the head region because the head detection has a low detection rate compared to the body detector and less accuracy for similarity match compared to the face match.

Overall, the exemplary embodiments mainly rely on face matches and location matches of bodies to track persons across frames, while body, head, face are connected using location information within a same frame.

Regarding frame fusion, as mentioned above, $F^3S$ uses both, visual (RGB) and thermal sensors to achieve high accuracy and high throughput fever screening. The system detects persons on the visual frames and then finds the temperature of the person from the thermal frame. To do this, a mapping from the visual frame to the thermal frame is required, that is, for a given point $(x_v, y_v)$ in the visual frame, what is the corresponding point $(x_t, y_t)$ in the thermal frame. Now, $(x_v, y_v) = (x_t, y_t)$ if the sensors have the exact same viewpoint. However, even though these sensors are assembled in a single unit, they are placed side-by-side, with a discernible distance between them. Such a setup introduces a difference in the sensor viewpoints, which implies that $(x_v, y_v) \neq (x_t, y_t)$. Instead, the points are related through a function—$(x_v, y_v) = f_{align}(x_t, y_t)$.

The system needs to estimate $f_{align}$ so that a point from the visual frame can be mapped to the correct point in the thermal frame to read the associated temperature.

Regarding a manual offset approach, due to physical displacement of visual and thermal sensors, there is no direct pixel-wise correlation between the output of the two sensors. The sensor outputs are related to each other with a combination of translation, scaling, rotation, shearing, projection due to different optical properties of sensors and mechanical alignments.

One of the simple ways to get approximate alignment is to perform static scaling and translation. For example, let $I_V$ be visual sensor data, $I_T$ be thermal sensor data and $I_{AT}$ be thermal sensor data aligned to the visual image. Then the alignment function $f_{align}$ can be defined as follows (where tx is a horizontal offset, ty is a vertical offset, Sx is a horizontal scale factor and Sy is a vertical scale factor).

$$f_{align} = \begin{bmatrix} 1 & 0 \\ 0 & 1 \\ t_x & t_y \end{bmatrix} * \begin{bmatrix} S_x & 0 \\ 0 & S_y \end{bmatrix}$$

With the above transformation function, it is possible to get temperature measurements in known areas of the visual ROI using data from $I_{AT} = f_{align}(I_T)$.

However, this approach produces correct alignment only for a shallow depth plane, and approximate alignment for neighboring pixels in that area of that plane. This approach does not align the entire frame. Pixels representing depth planes further or much closer from the correctly aligned image plane have larger misalignment. Alignment errors can be about 100+ pixels (in both the x and y direction) when the person is closer or further to camera. This leads to decreased accuracy, when temperature readouts are performed on thermal frames with reference to a forehead area inferred from the visual frame.

Regarding dynamic frame alignment, thermal imaging sensors have recommended measurement zones which usually start from about 3 feet from the sensor and spans all the way up to about 10 feet. If the function $f_{align}$ doesn't accurately capture the geometric distortion introduced by the placement of sensors and their spatial orientation, it leads to severe accuracy issues caused by reading temperatures from incorrect locations in the thermal image. Relative distortion between sensor images varies depending upon the depth plane. As the person walks toward the camera, multiple temperature readings have to be taken to take into account head and face poses, as well as occlusion with other persons and objects. Since the usual width of free flow traffic is about 6 to 8 feet wide and with horizontal field of view angle spans of about 90 degrees or more (due to measurement zone constraints), it leads to varying misalignment in the horizontal plane as the persons are found off the camera's optical axis.

However, alignment issues have been reported with the above methods. This calls for adaptive alignment of visual and thermal sensor data at different depths and different positions in the same image plane, as presented in the exemplary embodiments. Adaptive alignment needs to be performed for every person seen in the field of view, but it is difficult with the lack of depth information. It is theoretically possible to construct a 3D thermal model using static calibration of thermal and visual sensors followed by extraction of conjugate features and structure from motion (SfM) and the creation of a dense point cloud. Temperature information can be projected on the point cloud to generate a 3D thermal model. This, however, is time consuming to be realizable in real-time (100's of seconds per frame) and it is highly resource consuming.

Instead, the exemplary system $F^3S$ uses a different approach, as mentioned in Algorithm 2, reproduced below, to adapt the alignment of the thermal data with the visual data for all people seen in the field of view at various depth planes and horizontal displacements with reference to the optical axis. Algorithm 2 is therefore the dynamic frame alignment algorithm.

Figure 3:
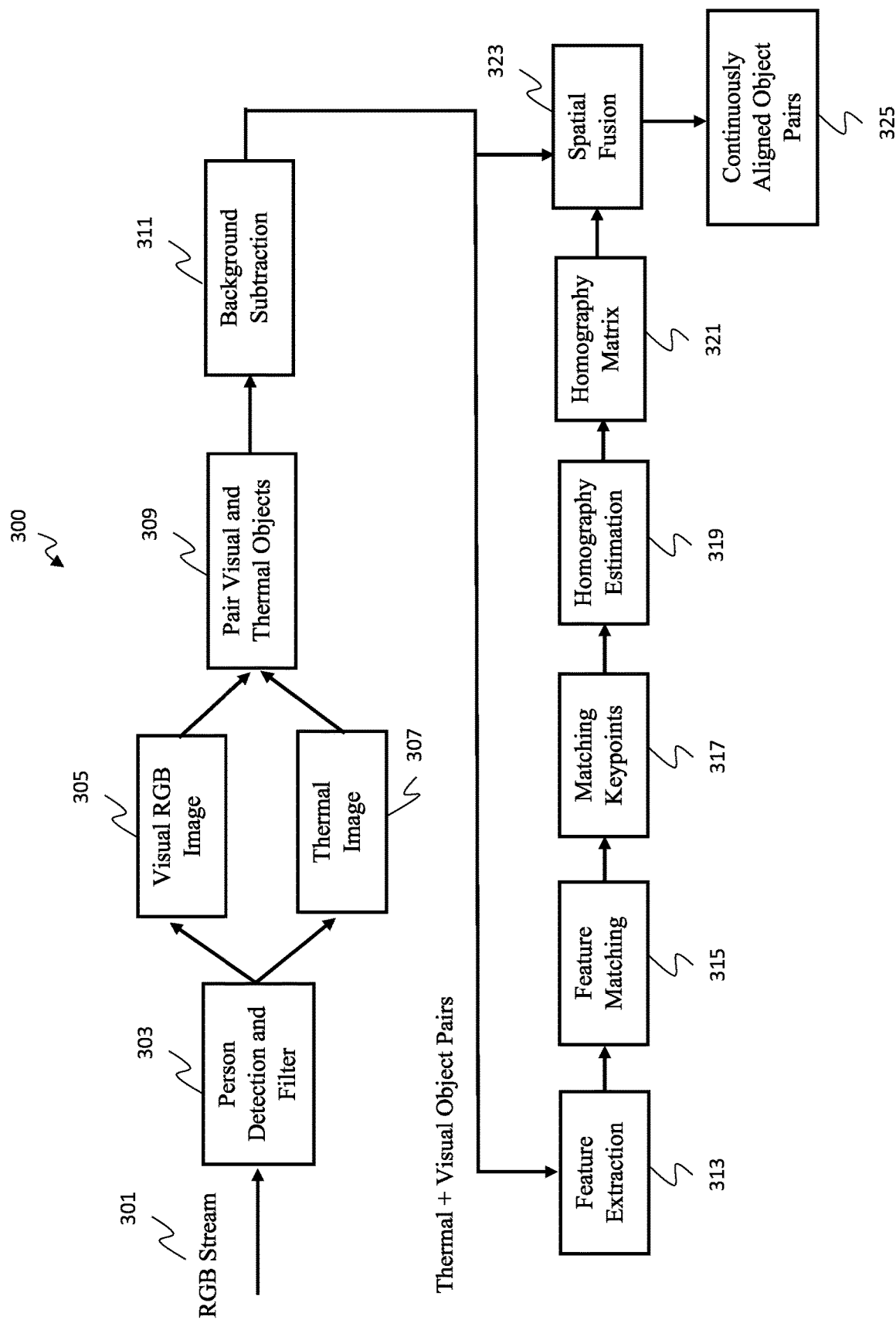
FIG. 3 is a block/flow diagram of an exemplary dynamic frame alignment configuration, in accordance with embodiments of the present invention.

Operational flow 300 to extract precisely aligned visual and thermal image pairs for all people in field of view is depicted in FIG. 3. The RGB stream 301 is processed by a person detector and filter 303 that extracts visual images 305 and thermal images 307 to create visual/thermal object pairs 309. The visual/thermal object pairs 309 are provided to a background subtraction component 311 where background is estimated in the images 305, 307 and subtracted. Next feature extraction 313, feature matching 315, matching keypoints 317, and homography estimation 319 are executed to generate a homography matrix 321. Spatial fusion 323 is performed such that continuously aligned object pairs 325 are provided.

As mentioned earlier, all the people entering the field of view are detected and tracked using body, head and face detection and tracking. Subject candidates for measurement are selected using a filtering criterion based on the bounding box geometries, so that measurement is performed only in the recommended zone. Once the target candidates are identified, the closest bounding box in the thermal sensor data is identified and thermal/visual head object pairs are created. These pairs will most likely be misaligned due to sensor artifacts. Most of the customer locations where the fever screening is performed, are closer to the entrance of the facility and most of the people are wearing sunglasses, head covering and face masks. To ensure free flow and during pandemic situations, security guard cannot stop and ask everyone to remove occluding objects from the head area. Misalignment in object pairs causes temperature readouts of sunglasses (which can be hot or reflective), face masks, head coverings or background, which leads to false alerts, which severely impedes movement or free flow of people. To ensure that all the object pairs in different depth planes and displacements from the optical axis are corrected, each object pair has to be aligned separately and automatically in real-time. Since thermal images have limited features to extract and limited correlation to the visual images, features in the boundary of a person's head are matched in the visual and thermal spectrum. To do this, the background is estimated in the images and subtracted and the foreground mask is obtained. ORB features of the foreground mask are obtained and matched using a brute force Hamming matcher to identify matching feature points. Using the matching feature points with a high confidence score across both pairs, a Homography matrix is obtained for each pair. Object pairs are rectified with respect to each other using a Homography matrix in the spatial fusion module/component (or spatial fuser).

```
Data: visualImagePersonBoundingBox
Result: Aligned thermal and visual person image pairs
objectPairs ← [];
thermalImagePersonBoundingBox ← [];
foreach visualImagePersonBoundingBox do
|    filterPersons(visualImagePersonBoundingBox,
|        headSize, faceSize, bodySize)
|    thermalROI ←
|        findClosest(thermalImage, visualImagePersonBoundingBox)
|    objectPairs ← [visualImagePersonBoundingBox,
|        thermalROI];
end
foreach objectPairs do
|    backgroundPair ← estimateBackground(objectPair);
|    imageMaskPair ←
|        computeMask(objectPair, backgroundPair);
|    maskFeature ← computeFeatures(imageMaskPair)
|    matchingFeatures ← matchFeatures(maskFeature,
|        filterCriterion)
```

```
|    homography ←
|        computeHomography(matchingFeatures)
|        objectPair ← spatialFusion(homography,
|            objectPair);
end
return objectPairs
```

Regarding fever screening, once visual and thermal frame fusion is completed, the fever-screening module/component then processes the fused frame to detect people having a fever. To measure the temperature of a person, the exemplary embodiments set up something referred to as a capture zone, that is, a zone in which the exemplary embodiments capture individuals and start temperature measurements when they enter the capture zone and stop when they leave the capture zone. A capture zone can be between 5 to 9 feet from the camera. By setting a capture zone, the exemplary embodiments avoid measuring temperatures of individuals who are too far from or too near the camera.

Along with the capture zone, the exemplary embodiments also configure a Region of Interest (ROI) within the frame. This region can be used to tightly control the region within the frame where the temperature measurements of individuals are taken. Note that within the ROI, people may be too far or too near, that is, may be within or outside the capture zone.

Algorithm 3, reproduced below, shows the procedure followed in determining the temperature of individuals as they walk through, e.g., an entrance of a building. Thus, algorithm 3 is a fever screening algorithm. The first step is to determine if the received fused frame is following the previous frames and is received in order, that is, the timestamp of the received frame is later than the previously received frame timestamp. Frames may sometimes be received out-of-order in rare cases, where due to minor glitches in network, an old frame may be delivered much later that the latter frames. To avoid any inconsistent results, frames that are received out-of-order are discarded. Next, all detected persons who lie outside the configured ROI are removed. To determine if a person is within or outside the ROI, the overlap between the bounding boxes of detections (body, head and face) of the person and the ROI is checked. If they completely overlap, then the person is considered to be within the ROI, otherwise the person is considered to be outside the ROI, and, therefore, discarded.

```
Data: Fused stream
Result: Temperatures for detected people
discardIfFrameOutOfOrder();
discardPersonsOutsideROI();
/* process detected persons                           */
foreach detected person within ROI do
|    if person within capture zone then
|    |    if person present in cache then
|    |    |    measureTemperatureAndUpdateInCache();
|    |    else
|    |    |    if person entered capture zone then
|    |    |    |    measureTemperatureAndAddInCache();
|    |    |    end
|    end
end
/* render frame with temperature annotations          */
renderFrameWiihAnnotations();
/* calculate/revise temperature and send alert        */
sendTemperatureAlert();
/* remove expired cache entries */
removeExpiredfromCache();
```

After removal of any person outside the ROI, the remaining individuals are processed one by one. The first check that is performed is to determine if the person is within the capture zone. If the person has come too close, and left the capture zone, the exemplary embodiments move on to the next individual without any further processing for this individual. The exemplary embodiments use metrics related to the various detections of the person (body, head and face) to determine if the person has come too close and left the capture zone. Dimensions of these bounding boxes become larger and larger as the person comes closer to the camera. After a certain configured value, the dimensions of bounding boxes become large enough to consider that the person has come close enough and left the capture zone.

If it is determined that the person is within the capture zone, then the next check is to determine if the person is already seen before or not. Fever-screening module/component maintains a cache of recently seen individuals to maintain the history of the individual as he/she enters the capture zone and then leaves the capture zone. The tracking id of the individual is used as an identifier to determine if the person is new or previously seen. If the tracking id is present in the cache, then the person is considered to be previously seen, otherwise the person is considered to be new. For a previously seen person, the new temperature reading is measured for the current frame and updated in cache corresponding to the tracking id of the individual. For a new person, a check is performed to determine if the person has entered the capture zone. Again, as before, the exemplary methods use the metrics related to various detections of the person (body, head and face) to determine if the person has come within the capture zone. The dimensions of these bounding boxes when the person is too far is small and as the person walks through and enters the capture zone, the dimensions continue to increase and after a certain configured value, the dimensions become large enough to consider that the person has entered the capture zone. If it is determined that the person has entered the capture zone, then the temperature for the person is measured and a new person with a new tracking id is added in the cache. Note that the temperature for a person is added or updated in cache only if it is within the acceptable human temperature range, to avoid any spurious temperature readings. Also, note that the exemplary embodiments start temperature measurements for an individual when he/she enters the capture zone and continue to be monitored and measured until the individual leaves the capture zone. Minimum and maximum dimensions of bounding boxes for detections (body, head and face) are configured to determine if the person has entered or left the capture zone.

After all individuals are processed, the frame is annotated with the temperatures for individuals and rendered, so that the operator can see the live view of the feed with temperatures of individuals annotated on the live stream. Setting the capture zone and ROI aids in keeping the rendered frame with annotations clutter-free, thus making it easy for the operator to see the temperatures of individuals. Without these, the temperatures would be captured for everyone within the frame and too many annotations might show up and throw-off the operator.

After rendering of the frame is complete, all individuals in the cache are processed one by one to determine the temperature for the individual across multiple readings and to send an alert or notification if the measured temperature is above a predetermined threshold and to remove any expired entries from cache, that is, remove any individuals in cache after a predetermined period of time, after they have left.

Regarding measurement of temperature within a frame, Algorithm 4, reproduced below, shows the procedure followed to measure the temperature for a person within a frame. Thus, Algorithm 4 is the prioritized temperature measurement algorithm. Highest priority is given to temperature measurements at the eye region, followed by the face region and finally the head region. Within each of these regions, a configurable or predefined or predetermined area is chosen and temperatures of pixels within that area is obtained from thermal sensor data. Among all the temperature values in the area, the maximum among those is chosen as the raw measured temperature. The exemplary embodiments choose the maximum value to avoid a false negative, e.g., missing an individual who might have a fever.

$$\text{slope} = (y_2 - y_1)/(x_2 - x_1) \quad \text{(equation 1)}$$

$$\text{intercept} = y_2 - \text{slope} * x_2 \quad \text{(equation 2)}$$

$$\text{core} = \text{slope} * \text{skin} + \text{intercept} \quad \text{(equation 3)}$$

---

Data: Person detection within fused frame
Result: Core body temperature for the person
temperature ← 0.0;
measured ← false;
if person has face detection then
| if face has eye detection then
| | temperature ← getTemperatureAtEyeRegion();
| | measured ← true;
| else
| | temperature ← getTemperatureAtFaceRegion();
| | measured ← true;
| end
end
if NOT measured AND person has head detection then
| temperature ← getTemperatureAtHeadRegion();
| measured ← true;
end
if measured then
| temperature ← getCorrectedTemperature();
end
return temperature

---

The raw measured temperature value is then corrected to obtain core body temperature. For this, the skin-to-core body temperature mapping provided by the thermal camera is used to obtain the core body temperature of the person. This mapping between skin temperature and core body temperature is provided by the thermal camera for a discrete set of temperature points and within a particular range. This provides multiple line segments where one end of the segment $x_1, y_1$ denotes the mapping between skin to core temperature at one discrete point and another end of the segment $x_2, y_2$ denotes the mapping at the next discrete point. For each of these line segments, the exemplary embodiments calculate the slope using equation 1 above and the intercept using equation 2 above.

Now, for a measured skin temperature reading for a person, the exemplary embodiments first identify the line segment that it belongs to, and then use slope and intercept data corresponding to this line segment and use equation 3 above to obtain the core body temperature for the person. If the measured skin temperature lies outside the available line segments, then the slope and intercept values of the closest line segment are used to obtain the core body temperature.

Regarding measurement of temperatures across frames and alerting, as an individual walks through the capture zone, multiple temperature readings of the person are recorded across frames (sequential or consecutive). Based on these readings, Algorithm 5 shows the procedure followed to calculate a person's temperature across frames along with the alerting mechanism. Thus, Algorithm 5 is the prioritized refinement and alerting algorithm. In order to measure the temperature for a person across frames, the exemplary embodiments compute a configurable number of minimum readings for the person to avoid any spurious measurements. Once the minimum number of readings are present for a person, the maximum temperature across the readings for different regions of the body (eye, face and head) is calculated. As previously mentioned, highest priority is given to the eyes, followed by the face and head, in determining the temperature of the person. Maximum temperature for the available highest priority region is recorded as the temperature for the person. Here too, to avoid any false negatives, that is, miss a person with fever, the exemplary embodiments choose to go with the maximum value of the temperature readings.

---

Data: Cache
Result: Temperature measurement and alerting
foreach cache entry do
| if minimum number of readings present then
| | max_head_temperature ←
| |   getMaxHeadTemperatureReading();
| | max_face_temperature ←
| |   getMaxFaceTemperatureReading();
| | max_eye_temperature ←
| |   getMaxEyeTemperatureReading();
| | if higher priority region temperature is available
| | then
| | | updatePersonTemperatureWithHigherPriorityReading();
| | else
| | | updatePersonTemperatureReading();
| | end
| end
| delta_temperature_increase ←
|   getDeltaTemperatureIncreased();
| if person temperature greater than configured threshold
|   AND delta_temperature_increase greater than
|   configured delta change OR higher priority region
|   temperature is available then
| | /* send alert                                    */
| | sendAlert();
| end
end

---

After the temperature is measured for the person, delta increase in temperature, that is, the difference between currently measured temperature and temperature for previously reported alerts for the person, if any, is calculated. An alert or notification is sent if the temperature of the person is greater than the predetermined threshold and the delta increase is greater than a configured delta change or if the region of current temperature measurement has a higher priority than a previously reported alert for the person. This procedure ensures that the first time a fever is detected for the person, the operator gets notified right away. After that, if temperature readings in a higher priority region are measured, those gets reported too, indicating a revised and potentially more accurate measured temperature for the person. This way, if a person was initially incorrectly detected with fever, $F^3S$ will automatically correct it by revising it and issuing an updated alert for the same individual. Any successive alerts for the same individual are sent only if the delta increase in temperature compared to a previously reported temperature, is greater than the configured delta change value. By using the tracking id of the person to identify multiple readings for a person, and by increasing the configuration for the delta change in temperature to issue an alert, repeated alerts for the same individual can be suppressed.

Figure 4:
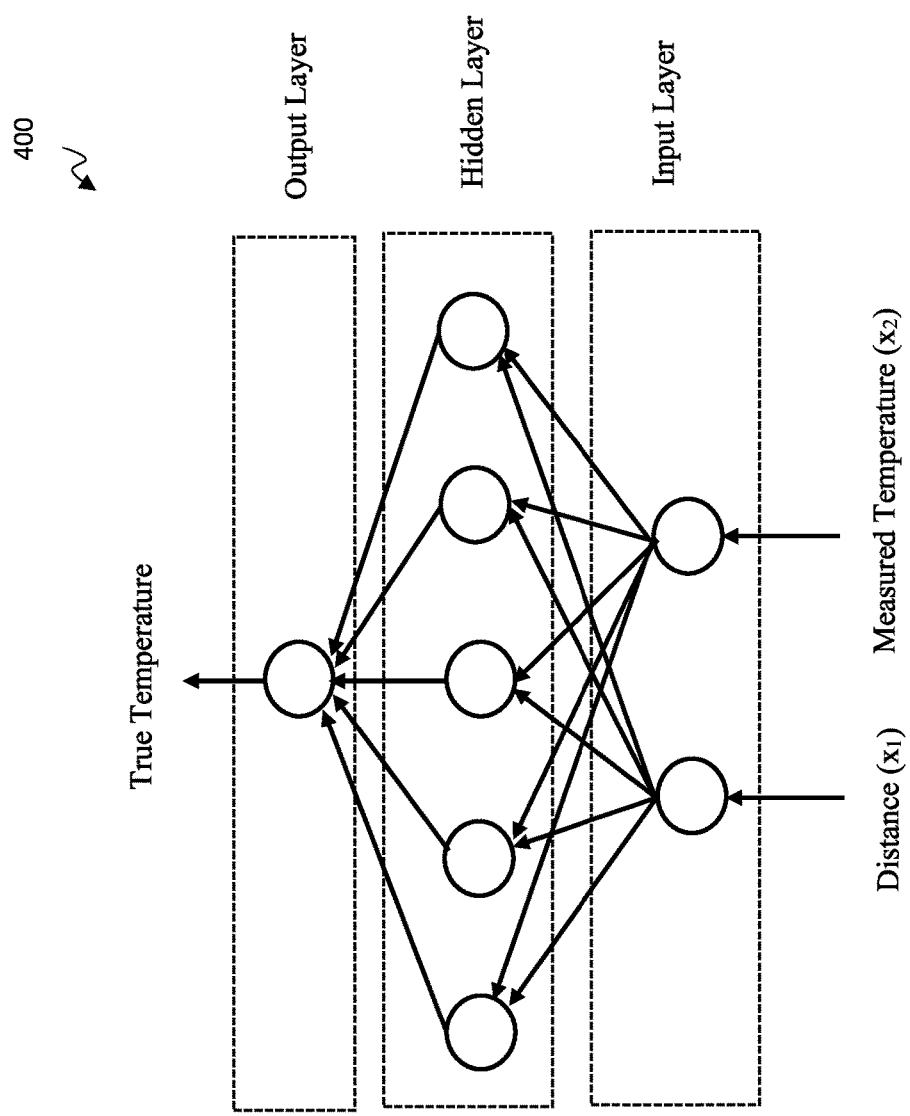
FIG. 4 is a block/flow diagram of an exemplary distance compensation model, in accordance with embodiments of the present invention.

FIG. 4 is a block/flow diagram 400 of an exemplary distance compensation model, in accordance with embodiments of the present invention.

Regarding distance correction, the measured temperature of an individual varies depending on the distance from the camera. This variation is non-linear. To correct for this variation in measured temperature with distance, the exemplary methods employs a neural network based distance compensation model, which can be used when a black body is present as part of the deployment. The model is a feed-forward neural network, to which the input parameters are the distance and the corresponding measured temperature at that distance. At the time of training, the measured temperature at the black body is considered as the ground truth, that is, the true temperature of the person and the model is trained to predict true temperature at various distances as the person walks through. During inference, the output from the model is used to obtain the true temperature of the person at different distances.

Regarding skin-to-core body temperature correction, mapping provided by the thermal camera is used to obtain the core body temperature of the person based on the measured skin temperature.

Figure 5:
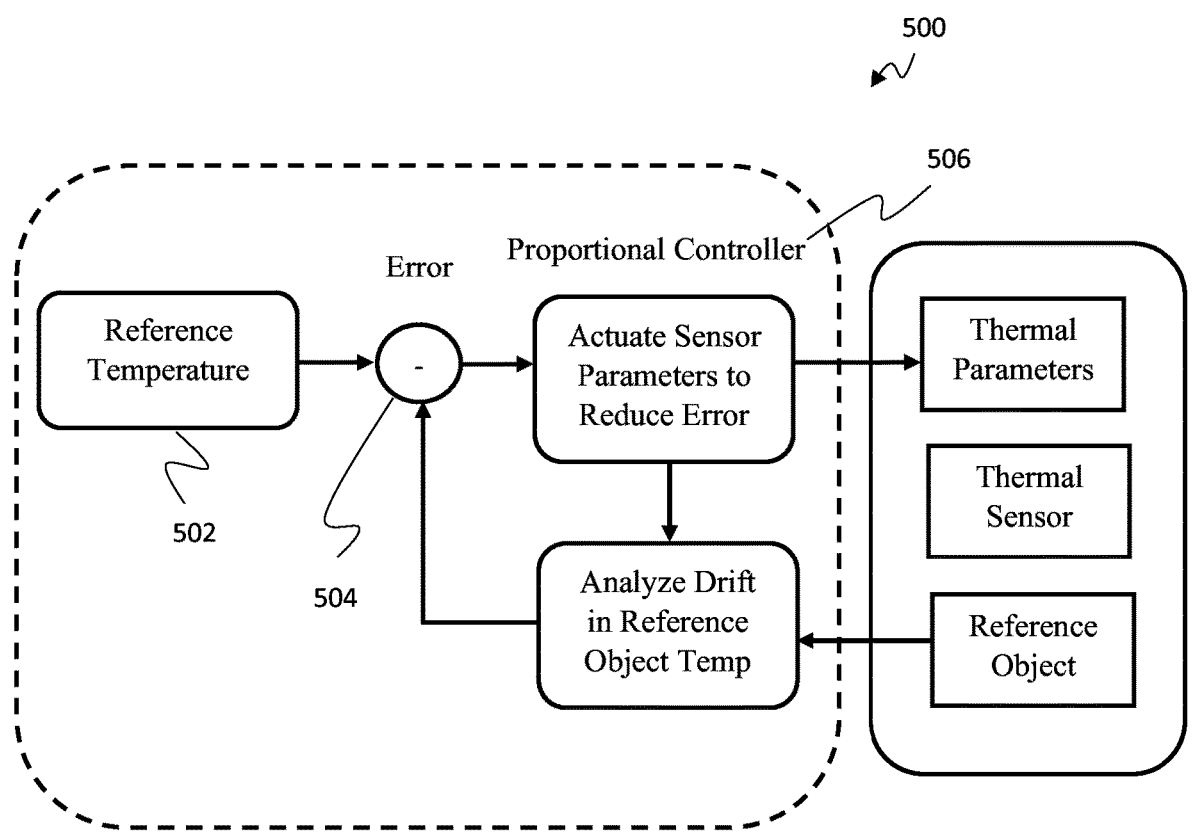
FIG. 5 is a block/flow diagram of an exemplary auto-calibration model, in accordance with embodiments of the present invention.

FIG. 5 is a block/flow diagram 500 of an exemplary auto-calibration model, in accordance with embodiments of the present invention.

As the environmental conditions change, the thermal readings from the camera start to drift from the actual temperature, thus producing incorrect temperature readings, which ultimately results in incorrect temperature measurements for individuals. Camera vendors provide several parameters to calibrate and correct for this drift and maintain the original temperatures. This correction however must be done manually, which is not practical to do in a real deployment where environmental conditions may change frequently. To do this automatically, the exemplary methods automatically detect the change and quickly adjust the camera parameters to maintain accurate temperature readings produced by the camera.

To detect the change automatically, a black body is used as a reference object and set to a known reference temperature 502 in the field of view of the camera. The temperature readings coming from the region of the black body are continuously monitored and any change in the temperature reading beyond an acceptable threshold is detected in real-time and immediate action is taken to adjust the camera parameters until the temperature of the black body is back to the reference temperature 502.

The drift, that is, error 504, in the temperature of the black body is measured in real-time and if the error 504 is beyond an acceptable threshold, then the dynamic proportional controller 506 corrects various parameters of the camera to iteratively reduce the error 504 and bring back the measured temperature of the black body to the reference temperature 502. Using this auto-calibration technique, even if the environmental conditions change, the camera always produces correct thermal readings, which ultimately results in correct temperature measurements for individuals.

In summary, in this invention, the exemplary embodiments present a rapid, contactless and hygienic fever screening system for demanding, free-flow and high-throughput environments. The solution measures in real-time the core body temperatures of multiple individuals in a free flow setting by using a camera with thermal and visual imaging.

Advantages of the exemplary embodiments of the present invention include at least a free flow fever screening system, which enables real-time, high-throughput measurement of core body temperature of individuals from a distance without any human intervention. Techniques are presented to fuse thermal and visual frames to enable accurate temperature measurements of multiple individuals simultaneously within and across frames. Techniques are presented to prioritize temperature measurements depending on visibility of different regions (eye, forehead, face and head) and to correct the measured temperature to obtain the true temperature of individuals. Further techniques are presented to track the temperature of individuals across frames and prioritize, collate, and filter alerts for the same individual. Additional techniques are presented to measure the temperature of individuals even when their face is partially covered, e.g., if they are wearing masks, sunglasses or hats.

Moreover, inventive features include at least dynamic association of semantically-equivalent regions across visual and thermal frames by using a dynamic alignment technique that analyzes content and context in real-time, tracking people through occlusions, identifying the eye and forehead, face and head regions where possible, and providing an accurate temperature reading by using a prioritized refinement algorithm, and robustness of measurement even in the presence of personal protective equipment like masks, or sunglasses or hats, all of which can be affected by hot weather and lead to spurious temperature readings.

In conclusion, the exemplary embodiments of the present invention perform rapid, contactless, and hygienic fever screening in real-time for demanding, free-flow and high-throughput environments, combine data from visual and thermal imaging to measure the temperature of an individual, adaptively align visual and thermal frames at different depths and different positions within the image plane, and map data from visual frames to thermal frames for multiple object pairs in the two frames. The exemplary embodiments of the present invention further match feature points across visual and thermal frames and determine a homography matrix, which is used for aligning object pairs, obtain depth/distance of a person from the camera using thermal and visual data feeds, identify and track a person across multiple frames, identify various regions and get corresponding temperatures from the thermal data, automatically adjust to changing environmental conditions where the temperature readings can start drifting from the actual temperature, and automatically calibrate thermal sensors to produce correct thermal readings by using a black body as a reference object. The exemplary embodiments of the present invention further measure the temperature of individuals only when they are in the capture zone and are within the configured region of interest, measure the temperature of individuals even when their face is partially covered, e.g., if they are wearing masks, sunglasses or hats, prioritize temperature measurement for different regions (eye and forehead, face and head) for an individual within a frame, prioritize and refine the temperature measurements for an individual across frames, and correct temperatures at a particular distance, based on a neural-network based distance compensation model. The exemplary embodiments of the present invention further obtain true temperatures of an individual based on the measured temperature, determine when to send temperature alerts or notifications for an individual, suppress repeated temperature alerts for the same individual, avoid spurious temperature measurements for an individual, and collect enough measurements before determining the temperature of an individual.

Figure 6:
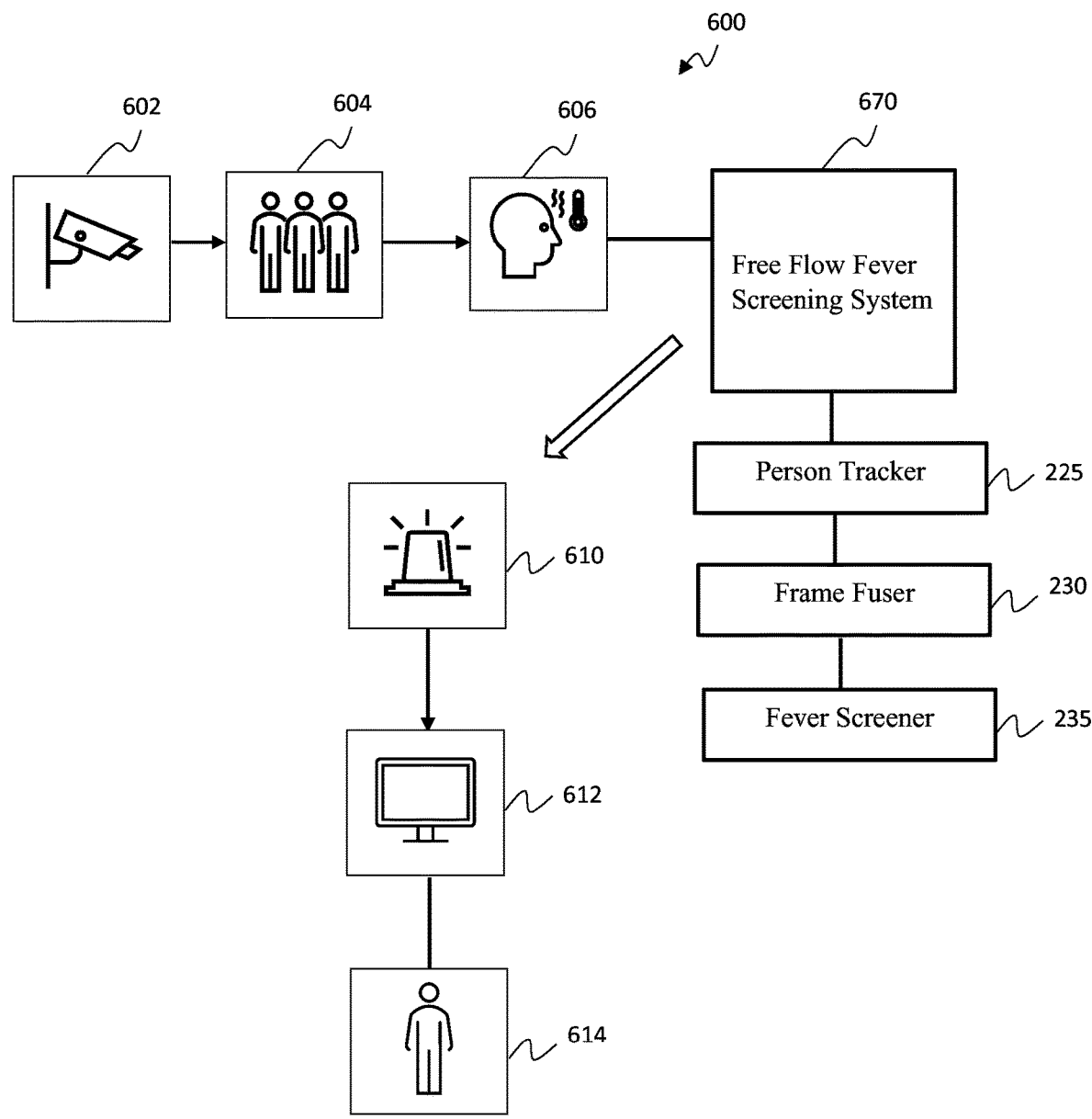
FIG. 6 is a block/flow diagram of a practical application of the free flow fever screening system, in accordance with embodiments of the present invention.

FIG. 6 is a block/flow diagram 600 of a practical application of the free flow fever screening architecture, in accordance with embodiments of the present invention.

In one practical example, one or more cameras 602 capture a plurality of individuals 604 in a free flow setting. An individual 606 from the plurality of individuals 604 is detected to have a fever. The free flow fever screening system 670 is implemented to detect individuals having a fever in a free flow setting by implementing a person tracker 225, a frame fuser 230, and a fever screener 235. The free flow fever screening system 670 can trigger an alert or notification 610 provided or displayed on a user interface 612 handled by a user or operator 614. The operator 614 can then notify someone within the vicinity of the individual 606 to approach and isolate such individual 606 for further medical evaluation.

Figure 7:
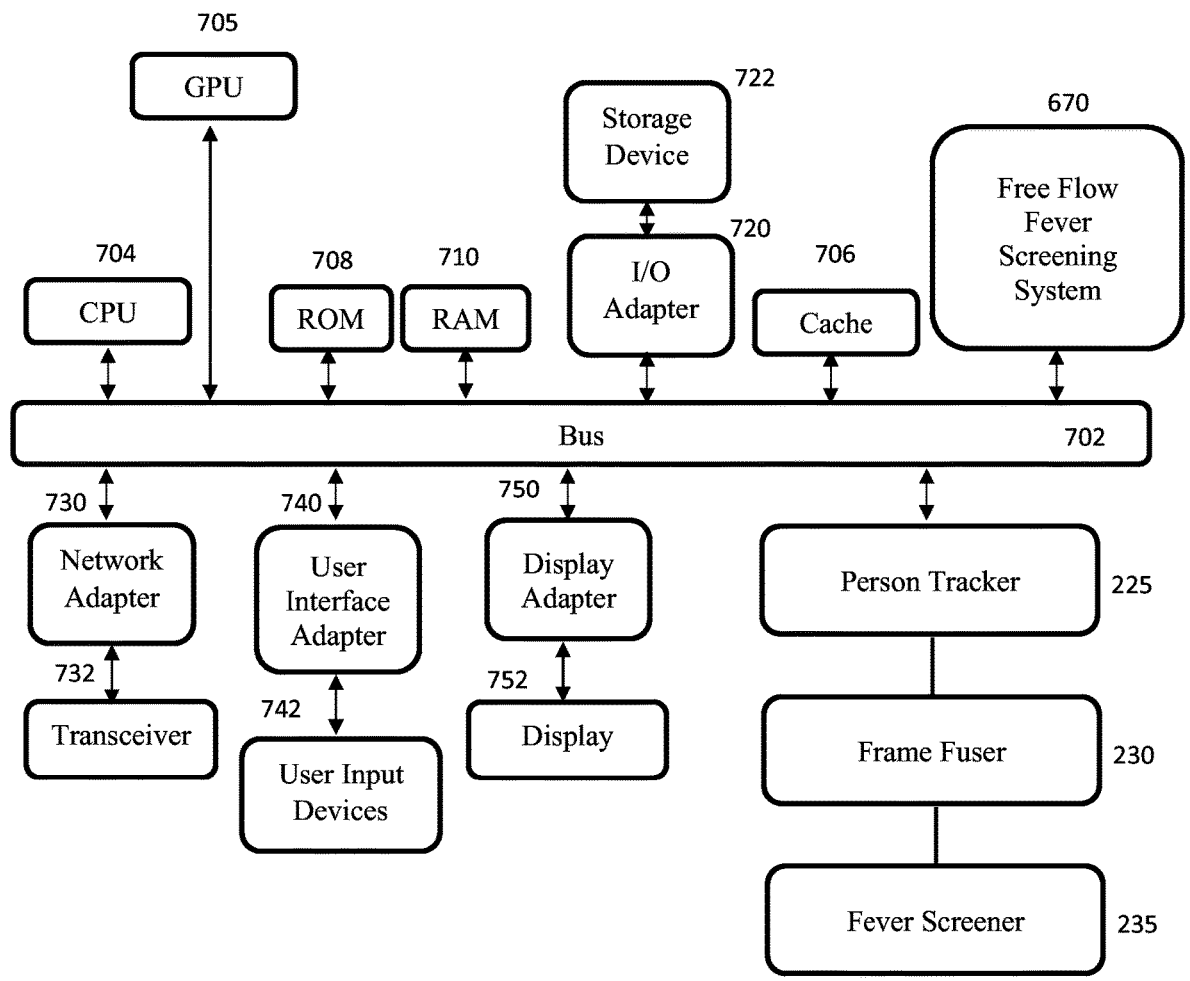
FIG. 7 is an exemplary processing system for the free flow fever screening system, in accordance with embodiments of the present invention.

FIG. 7 is an exemplary processing system for the free flow fever screening architecture, in accordance with embodiments of the present invention.

The processing system includes at least one processor (CPU) 704 operatively coupled to other components via a system bus 702. A GPU 705, a cache 706, a Read Only Memory (ROM) 708, a Random Access Memory (RAM) 710, an input/output (I/O) adapter 720, a network adapter 730, a user interface adapter 740, and a display adapter 750, are operatively coupled to the system bus 702. Additionally, a free flow fever screening system 670 can be employed that includes a person tracker 225, a frame fuser 230, and a fever screener 235.

A storage device 722 is operatively coupled to system bus 702 by the I/O adapter 720. The storage device 722 can be any of a disk storage device (e.g., a magnetic or optical disk storage device), a solid-state magnetic device, and so forth.

A transceiver 732 is operatively coupled to system bus 702 by network adapter 730.

User input devices 742 are operatively coupled to system bus 702 by user interface adapter 740. The user input devices 742 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 742 can be the same type of user input device or different types of user input devices. The user input devices 742 are used to input and output information to and from the processing system.

A display device 752 is operatively coupled to system bus 702 by display adapter 750.

Of course, the processing system may also include other elements (not shown), as readily contemplated by one of skill in the art, as well as omit certain elements. For example, various other input devices and/or output devices can be included in the system, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system are readily contemplated by one of ordinary skill in the art given the teachings of the present invention provided herein.

Figure 8:
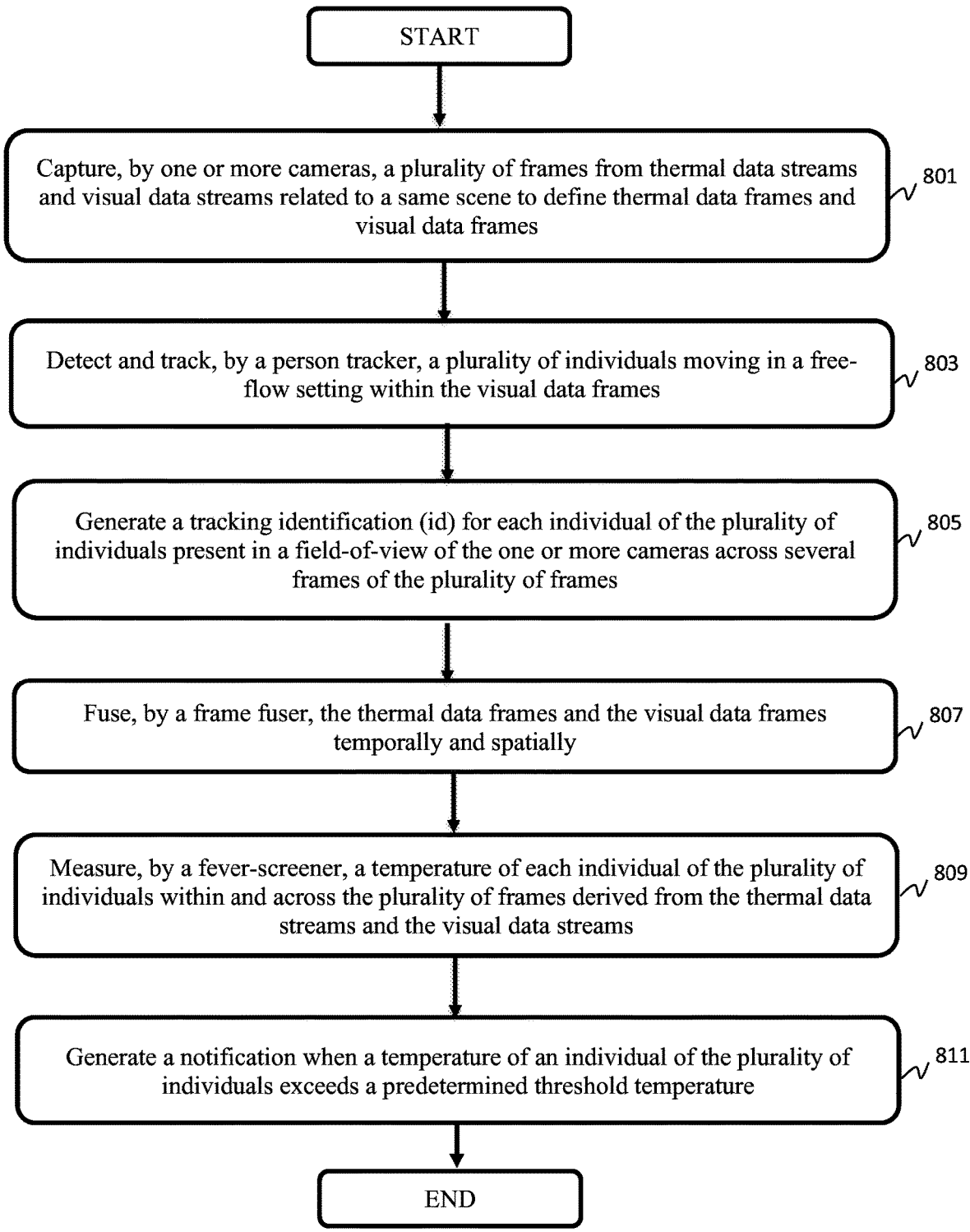
FIG. 8 is a block/flow diagram of an exemplary method for executing the free flow fever screening system, in accordance with embodiments of the present invention.

FIG. 8 is a block/flow diagram of an exemplary method for executing the free flow fever screening architecture, in accordance with embodiments of the present invention.

At block 801, capture, by one or more cameras, a plurality of frames from thermal data streams and visual data streams related to a same scene to define thermal data frames and visual data frames.

At block 803, detect and track, by a person tracker, a plurality of individuals moving in a free flow setting within the visual data frames.

At block 805, generate a tracking identification (id) for each individual of the plurality of individuals present in a field-of-view of the one or more cameras across several frames of the plurality of frames.

At block 807, fuse, by a frame fuser, the thermal data frames and the visual data frames temporally and spatially.

At block 809, measure, by a fever-screener, a temperature of each individual of the plurality of individuals within and across the plurality of frames derived from the thermal data streams and the visual data streams.

At block 811, generate a notification when a temperature of an individual of the plurality of individuals exceeds a predetermined threshold temperature.

As used herein, the terms "data," "content," "information" and similar terms can be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, the data can be received directly from the another computing device or can be received indirectly via one or more intermediary computing devices, such as, for example, one or more servers, relays, routers, network access points, base stations, and/or the like. Similarly, where a computing device is described herein to send data to another computing device, the data can be sent directly to the another computing device or can be sent indirectly via one or more intermediary computing devices, such as, for example, one or more servers, relays, routers, network access points, base stations, and/or the like.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," "calculator," "device," or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical data storage device, a magnetic data storage device, or any suitable combination of the foregoing. In the context of this document, a computer readable storage medium may be any tangible medium that can include, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks or modules.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks or modules.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks or modules.

It is to be appreciated that the term "processor" as used herein is intended to include any processing device, such as, for example, one that includes a CPU (central processing unit) and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc. Such memory may be considered a computer readable storage medium.

In addition, the phrase "input/output devices" or "I/O devices" as used herein is intended to include, for example, one or more input devices (e.g., keyboard, mouse, scanner, etc.) for entering data to the processing unit, and/or one or more output devices (e.g., speaker, display, printer, etc.) for presenting results associated with the processing unit.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for free flow fever screening by measuring core body temperature of individuals from a distance without human intervention, the method comprising:

capturing, by one or more thermal cameras, a plurality of frames from thermal data streams and visual data streams related to a same scene to define thermal data frames and visual data frames, wherein adaptive alignment is performed for thermal data frames and the visual data frames at different depths and different positions in a same image plane;

detecting and tracking, by a person tracker, a plurality of individuals moving in a free-flow setting within the visual data frames, wherein feature points are matched across the thermal data frames and the visual data frames to determine a homography matrix used for aligning thermal/visual object pairs;

generating a tracking identification (id) for each individual of the plurality of individuals present in a field-of-view of the one or more cameras across several frames of the plurality of frames;

fusing, by a frame fuser, the thermal data frames and the visual data frames temporally and spatially, the fusing comprising detecting each individual of the plurality of individuals in the visual data frames and determining the temperature of the each individual from the thermal data frames by estimating an alignment function $f_{align}$ by mapping from the visual data frames to the thermal data frames by $(x_v, y_v) = f_{align}(x_t, y_t)$, where $(x_v, y_v)$ represents a given point in the visual data frames and $(x_t, y_t)$ represents a corresponding point in the thermal data frames;

measuring, by a fever screener, a temperature of the each individual of the plurality of individuals within and across the plurality of frames derived from the thermal data streams and the visual data streams;

generating a notification when a temperature of a particular individual of the plurality of individuals exceeds a predetermined threshold temperature; and automatically correcting for variation in measured temperatures of the plurality of individuals by dynamically adjusting parameters of the thermal camera based on detected environmental changes, and performing error correction by comparing the measured temperatures of the plurality of individuals to a reference temperature source responsive to detecting deviations from expected temperature readings.

2. The method of claim 1, wherein a neural-network based distance compensation model is employed to correct for variation in measured temperature with distance and auto-calibration is employed to automatically correct for a drift error by using a dynamic proportional controller.

3. The method of claim 1, wherein the temporally fusing relates to fusing in a time domain and the spatially fusing relates to fusing in a space domain.

4. The method of claim 3, wherein the spatially fusing relates to mapping pixels between the thermal data frames and the visual data frames.

5. The method of claim 1, wherein the tracking id is used to identify a same individual across the several frames and to record a temperature reading of the identified individual in each of the several frames to create a cluster of temperature readings for the identified individual.

6. The method of claim 1, wherein the fever screener maintains a cache of each of the plurality of individuals with a corresponding tracking id and bounding boxes of detection, the bounding boxes defined for a body, a head, and a face of all of the plurality of individuals in each frame of the plurality of frames.

7. The method of claim 1, wherein the fever screener measures the temperature of each individual of the plurality of individuals in a capture zone and within a region of interest.

8. The method of claim 1, wherein the temperature measurements of each individual of the plurality of individuals within and across the plurality of frames is prioritized based on visibility of different regions of the individuals.

9. A non-transitory computer-readable storage medium comprising a computer-readable program for free flow fever screening by measuring core body temperature of individuals from a distance without human intervention, wherein the computer-readable program when executed on a computer causes the computer to perform steps of:

capturing, by one or more thermal cameras, a plurality of frames from thermal data streams and visual data streams related to a same scene to define thermal data frames and visual data frames, wherein adaptive alignment is performed for thermal data frames and the visual data frames at different depths and different positions in a same image plane;

detecting and tracking, by a person tracker, a plurality of individuals moving in a free-flow setting within the visual data frames, wherein feature points are matched across the thermal data frames and the visual data frames to determine a homography matrix used for aligning thermal/visual object pairs;

generating a tracking identification (id) for each individual of the plurality of individuals present in a field-of-view of the one or more cameras across several frames of the plurality of frames;

fusing, by a frame fuser, the thermal data frames and the visual data frames temporally and spatially, the fusing comprising detecting each individual of the plurality of individuals in the visual data frames and determining the temperature of the each individual from the thermal data frames by estimating an alignment function $f_{align}$ by mapping from the visual data frames to the thermal data frames by $(x_v, y_v) = f_{align}(x_t, y_t)$, where $(x_v, y_v)$ represents a given point in the visual data frames and $(x_t, y_t)$ represents a corresponding point in the thermal data frames;

measuring, by a fever screener, a temperature of each individual of the plurality of individuals within and across the plurality of frames derived from the thermal data streams and the visual data streams;

generating a notification when a temperature of an individual of the plurality of individuals exceeds a predetermined threshold temperature; and automatically correcting for variation in measured temperatures of the plurality of individuals by dynamically adjusting parameters of the thermal camera based on detected environmental changes, and performing error correction by comparing the measured temperatures of the plurality of individuals to a reference temperature source responsive to detecting deviations from expected temperature readings.

10. The non-transitory computer-readable storage medium of claim 9, wherein the temporally fusing relates to fusing in a time domain and the spatially fusing relates to fusing in a space domain.

11. The non-transitory computer-readable storage medium of claim 10, wherein the spatially fusing relates to mapping pixels between the thermal data frames and the visual data frames.

12. The non-transitory computer-readable storage medium of claim 9, wherein the tracking id is used to identify a same individual across the several frames and to record a temperature reading of the identified individual in each of the several frames to create a cluster of temperature readings for the identified individual.

13. The non-transitory computer-readable storage medium of claim 9, wherein the fever screener maintains a cache of each of the plurality of individuals with a corresponding tracking id and bounding boxes of detection, the bounding boxes defined for a body, a head, and a face of all of the plurality of individuals in each frame of the plurality of frames.

14. The non-transitory computer-readable storage medium of claim 9, wherein the fever screener measures the temperature of each individual of the plurality of individuals in a capture zone and within a region of interest; and wherein the temperature measurements of each individual of the plurality of individuals within and across the plurality of frames is prioritized based on visibility of different regions of the individuals.

15. The non-transitory computer-readable storage medium of claim 9, wherein a neural-network based distance compensation model is employed to correct for variation in measured temperature with distance and auto-calibration is employed to automatically correct for a drift error by using a dynamic proportional controller.

16. A system for free flow fever screening by measuring core body temperature of individuals from a distance without human intervention, the system comprising:
- one or more thermal cameras to capture a plurality of frames from thermal data streams and visual data streams related to a same scene to define thermal data frames and visual data frames, wherein adaptive alignment is performed for thermal data frames and the visual data frames at different depths and different positions in a same image plane;
- a person tracker to detect and track a plurality of individuals moving in a free-flow setting within the visual data frames, wherein feature points are matched across the thermal data frames and the visual data frames to determine a homography matrix used for aligning thermal/visual object pairs;
- a tracking identification (id) generated for each individual of the plurality of individuals present in a field-of-view of the one or more cameras across several frames of the plurality of frames;
- a frame fuser configured for fusing the thermal data frames and the visual data frames temporally and spatially, the fusing comprising detecting each individual of the plurality of individuals in the visual data frames and determining the temperature of the each individual from the thermal data frames by estimating an alignment function $f_{align}$ by mapping from the visual data frames to the thermal data frames by $(x_v, y_v) = f_{align}(x_t, y_t)$, where $(x_v, y_v)$ represents a given point in the visual data frames and $(x_t, y_t)$ represents a corresponding point in the thermal data frames; and
- a fever-screener to measure a temperature of each individual of the plurality of individuals within and across the plurality of frames derived from the thermal data streams and the visual data streams, wherein a notification is generated when a temperature of an individual of the plurality of individuals exceeds a predetermined threshold temperature, and variations in measured temperatures of the plurality of individuals are automatically corrected by dynamically adjusting parameters of the thermal camera based on detected environmental changes, and performing error correction by comparing the measured temperatures of the plurality of individuals to a reference temperature source responsive to detecting deviations from expected temperature readings.

* * * * *